(12) United States Patent
Deka et al.

(10) Patent No.: US 6,271,035 B1
(45) Date of Patent: Aug. 7, 2001

(54) METHODS AND COMPOSITIONS FOR RAPID STAINING OF NUCLEIC ACIDS IN WHOLE CELLS

(75) Inventors: Chiranjit Deka, Miami; Kristie M. Gordon, Coral Gables; Ravinder Gupta, Pembroke Pines; Allan Horton, Miami, all of FL (US)

(73) Assignee: Coulter International Corp., Miami, FL (US)

( * ) Notice: Subject to any disclaimer, the term of this patent is extended or adjusted under 35 U.S.C. 154(b) by 0 days.

(21) Appl. No.: 09/175,495

(22) Filed: Oct. 20, 1998

(51) Int. Cl.$^7$ ................................................. G01N 31/00
(52) U.S. Cl. ........................ 436/10; 436/8; 436/17; 436/63; 436/164; 436/166; 436/172
(58) Field of Search ..................... 436/63, 8, 10, 436/164, 166, 172, 17

(56) References Cited

U.S. PATENT DOCUMENTS

| | | |
|---|---|---|
| 3,962,125 | 6/1976 | Armstrong . |
| 4,883,867 | 11/1989 | Lee et al. . |
| 4,957,870 | 9/1990 | Lee et al. . |
| 5,284,771 * | 2/1994 | Fan et al. ............................. 436/10 |
| 5,360,739 | 11/1994 | Fan et al. . |
| 5,438,003 | 8/1995 | Colella et al. . |
| 5,496,734 * | 3/1996 | Sakata ................................. 436/63 |
| 5,563,070 | 10/1996 | Yamamoto et al. . |
| 5,633,167 | 5/1997 | Fan et al. . |
| 5,639,666 | 6/1997 | Shenkin . |
| 5,691,204 * | 11/1997 | Kim et al. ........................... 436/63 |
| 5,733,784 * | 3/1998 | Studholme et al. ................ 436/63 |
| 5,830,764 * | 11/1998 | Sorette .............................. 436/63 |
| 5,994,138 * | 11/1999 | Veriac ................................ 436/10 |
| 6,060,322 * | 5/2000 | Horton et al. ....................... 436/63 |

OTHER PUBLICATIONS

H. Shapiro, Practical Flow Cytometry, 3$^{rd}$ edit., Wiley–Liss, New York (1995).
Davis, et al., "Clinical Flow Cytometric Reticulocyte Analysis", *Pathobiology*, 58:99–106 (1990).
T.G. Hoy, "Flow Cytometry : clinical applications in haematology", *Bailliere's Clin. Haemat.*, 3:977–988 (1990).
H.J. Tanke, "Reticulocytes and Mature Erythrocytes", *Flow Cytometry in Hematology*, Chp. 2.1, pp. 75–93 (1992).
Vander, et al., "Reticulocyte counts by means of fluorescence microscopy", *J. Lab. Clin. Med.*, 62:132 (1993).
A.A. Thaer, "Microfluorometric Analysis of the Reticulocycte Population in Peripheral Blood of Mammals", *Cytology Automation*, DMD Evans (ed.), E&S Livingstone, Edinburgh (1970).
Seligman, et al., "Automated Analysis of Reticulocytes Using Fluorescent Staining with Both Acridine Orange and an Immunofluorescence Technique", *American J. Hematol.*, 14:57–66 (1983).
Lee, et al., "Thiazole Orange: A New Dye for Reticulocycte Analysis", *Cytometry*, 7:508 (1986).
Van Hove, et al., "Reticulocyte count using thiazole orange. A flow cytometry method",*Clin. Lab. Haemat.*, 12:287–299 (1990).
Carter, et al., "Counting reticulocytes by flow cytometry: use of thiazole orange", *Clin. Lab. Haemat.*,11:267–271 (1989).

* cited by examiner

*Primary Examiner*—Jill Warden
*Assistant Examiner*—Monique T. Cole
(74) *Attorney, Agent, or Firm*—Cathy A. Kodroff; Mitchell E. Alter

(57) ABSTRACT

A rapid fluorescence staining method for facilitating flow cytometry analysis of reticulocytes is described. The method comprises contacting cells with a cocktail containing a detergent, sphering agent, and a cell impermeable dye, such as TO-PRO-3, for about one minute. Advantageously, the inventors have found that the cocktail permits the dye to penetrate the cell membrane rapidly.

16 Claims, 4 Drawing Sheets

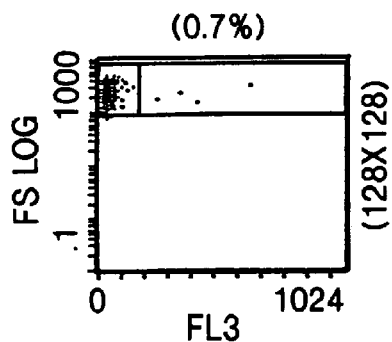
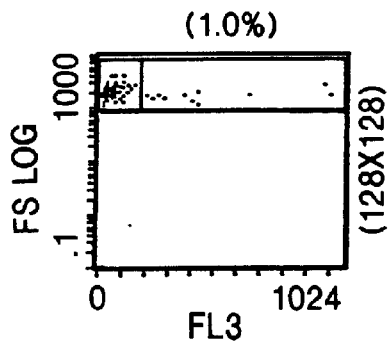
FIG. 3A
FIG. 3B
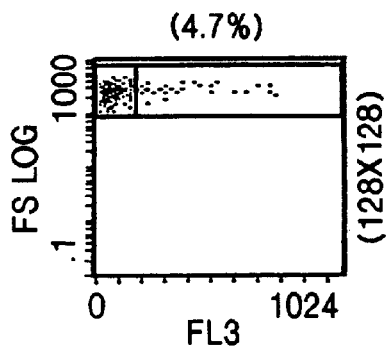
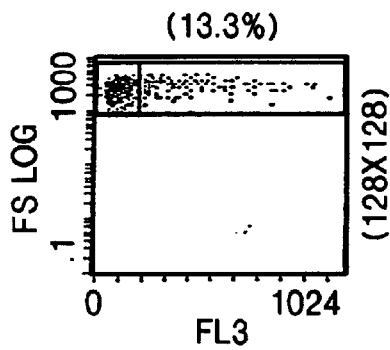
FIG. 3C
FIG. 3D
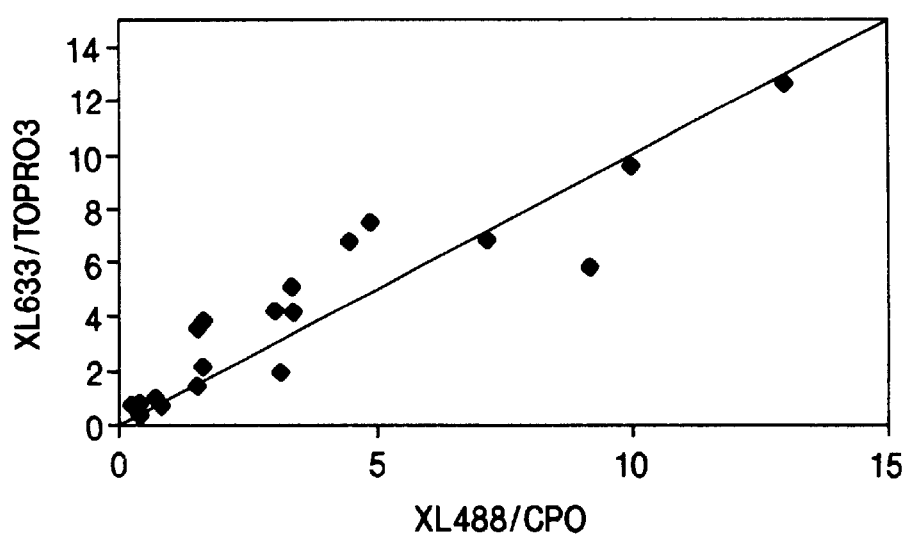
FIG. 4

METHODS AND COMPOSITIONS FOR RAPID STAINING OF NUCLEIC ACIDS IN WHOLE CELLS

FIELD OF THE INVENTION

The present invention relates generally to the field of detection and enumeration of nucleic acids by flow cytometry.

BACKGROUND OF THE INVENTION

Enumeration of reticulocytes, i.e., the most immature erythrocytes, in human peripheral blood is a valuable component of diagnostic hematology, useful in the diagnoses of hemorrhage, anemia, monitoring bone marrow transplantation, monitoring patients undergoing chemotherapy and other disorders involving blood cell production [U.S. Pat. No. 5,360,739; H. Shapiro, Practical Flow Cytometry, 3$^{rd}$ edit., 1995; Wiley-Liss, New York; Davis et al, (1990) *Pathobiol.*, 58:99–106; Hoy, (1990) *Bailliere's Clin. Haemat.*, 3:977–988; H. J. Tanke, "Reticulocytes and Mature Erythrocytes" in *Flow Cytometry in Haematology* (1992) Academic Press Ltd., pp. 75–93]. Because reticulocytes contain ribonucleic acid (RNA), if stained with RNA binding dyes, these cells fluoresce when illuminated by a light source of appropriate wavelength. RNA binding dyes have been used to distinguish reticulocytes from more mature red blood cells (RBCs).

Using fluorescence measurements, distribution of relatively large reticulocyte population can be determined by flow cytometry in a fast and reliable manner provided the cells are appropriately stained with a fluorescent dye. Two of the primary factors that determine the usefulness of a specific reticulocyte enumeration method are: (1) the fluorescence characteristics of the dye when bound to RNA, and (2) method of staining.

A fluorescent dye suitable for reticulocyte enumeration should ideally have bright fluorescence when bound to RNA and very little fluorescence when unbound to RNA. A staining method ideally should be fast, most preferably on the order of one minute or less, if a reticulocyte assay is intended for automated/routine hematology application. Matching the above two requirement has been at the core of research efforts in developing useful reticulocyte assays over the last several years [H. J. Tanke, Reticulocytes and Mature Erythrocytes" in Flow Cytometry in Haematology (1992) Academic Press Ltd.].

Prior art reticulocyte enumeration methods suitable for automated hematology is based on acridine orange or thiozole orange derivatives. Specific examples for Acridine Orange (AO) are cited in Vander et. al., (1993) J. Lab. Clin. Med, 62:132, Thaer et. el. (1970) "Microfluorometric analysis of the reticulocyte population in peripheral blood of mammals" in Cytology Automation, DMD Evans (ed.), E&S Livingstone, Edinburgh (1970), pp. 180–195; and Seligman et. al., (1983) American J. Hematol., 14:57–66], Thiazole Orange (TO) in Cytometry (1986) 7:508 L. G. Lee et. al.; U.S. Pat. Nos. 4,883,867 and 4,957,870; Van Hove et. al. (1990) Clin. Lab. Hemat., 12:287–299; Carter et. al. (1989) Clin. Lab. Haemat, 11:267–271], and coriphosphine-O (CPO) [U.S. Pat. No. 5,639,666]. AO, TO, CPO are all brightly fluorescent when bound to RNA. Each of these dyes are cell membrane permeant, i.e. they transport through the membrane of the reticulocyte cells freely. As a result, these dyes can stain the intra-cellular RNA in relatively short time. This makes them attractive and useful for automated hematology application. However, the AO and CPO suffer from a serious disadvantage in that they tend to stain non-specifically with most things that they contact, including tubing in a flow cytometer. This complicates measurements on cells because fluorescence from the non-specifically bound molecules interfere with RNA bound molecules. As for TO, its use is limited in that it can not be excited in the red wavelengths. This precludes it from being used for fluorescence based cellular analysis using low cost illumination sources such as diode lasers.

There have been research efforts to overcome the limitations presented by the above dyes by developing alternative nucleic acid staining dyes. As a result, there now exists a large number of nucleic acid binding dyes that have fluorescence properties which are least equivalent to those of AO, TO and CPO. Examples of such dyes such as TOTO-1, TOTO-3, YOYO-1, YOYO-3, TO-PRO-1, TO-PRO-3, propidium iodide (PI), ethidium bromide. Unfortunately, none of these dyes are cell membrane permeant. Prior art methods for reticulocyte enumeration using membrane impermeant dye Pyronin Y showed that cells must be fixed for 2 hrs or longer (up to 24 hours). This makes Pyronin Y unsuitable for automated hematology applications [H. J. Tanke, "Reticulocytes and Mature Erythrocytes" in *Flow Cytometry in Haematology* (1992) Academic Press Ltd., pp. 81]. A second prior art method using cell impermeant dyes such as TO-PRO-3 is described in U.S. Pat. No. 5,563,070. The method requires incubation of a dye in whole blood for at least 30 min. As a result, this method is not suited to automated hematology applications.

Thus, there exist a need in the art for composition and methods that enable rapid staining of intra cellular nucleic acid by normally membrane impermeant fluorescent dyes, and permit ready, accurate and reproducible enumeration of reticulocytes.

SUMMARY OF THE INVENTION

In one aspect, the present invention provides a method for facilitating rapid transport of dye molecules through cell membrane, thus permitting staining of intracellular nucleic acids. This method is particularly well suited for staining of reticulocytes. The method involves the steps of mixing the cells and a dye which is a relatively cell membrane impermeant dye with a neutral detergent and a sphering agent for about one minute prior to analysis, e.g., by flow cytometry.

In another aspect, the present invention provides a composition which facilitates transport of cell membrane impermeant nucleic acid dye through a cell membrane. Suitably, this composition contains a non-ionic detergent, a sphering agent, and cell membrane impermeant dye.

Other aspects and advantages of this invention will be readily apparent from the detailed description of the invention.

BRIEF DESCRIPTION OF THE DRAWINGS

FIG. 3A shows the fluorescence intensities for cells treated with TO-PRO-3 alone.

FIG. 3B shows the fluorescence intensities for cells treated with TO-PRO-3 in presence of the sphering agent.

FIG. 3C shows the fluorescence intensities for cells treated with TO-PRO-3 in presence of detergent Nonidet P-40.

FIG. 3D shows the fluorescence intensities for cells treated with TO-PRO-3 in presence of both the sphering agent and detergent Nonidet P-40.

FIG. 4 provides a comparison of reticulocyte percentages obtained for 20 different blood samples using TO-PRO-3 and CPO staining methods.

DETAILED DESCRIPTION OF THE INVENTION

Figure 1A:
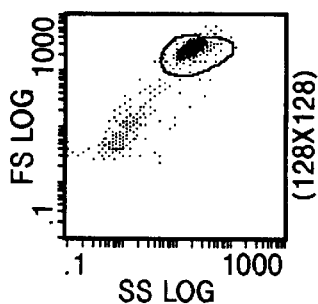
FIGS. 1A–1C show the fluorescence signals from reticulocytes for a sample having a high reticulocyte counts which has been stained with TO-PRO-3. The reticulocytes are resolved from the mature red cells by the high fluorescence signal from the RNA bound TO-PRO-3 (FIG. 1C). In one dimensional histogram, the stained reticulocytes appear as distinct tail on the right hand side (FIG. 1B) (retic count>12%).
Figure 1B:
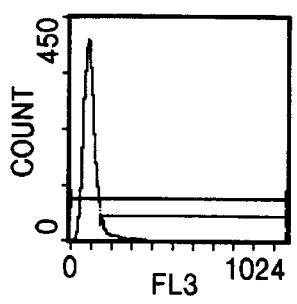
Figure 1C:
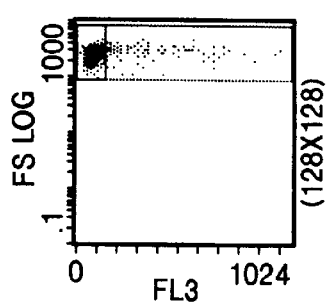
Figure 1D:
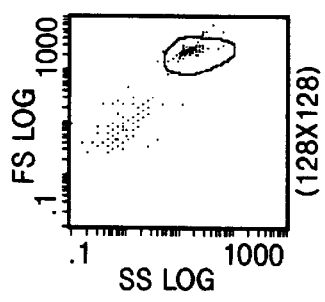
FIGS. 1D–1F show the fluorescence signals from reticulocytes for a sample having a low reticulocyte count using TO-PRO-3 fluorescence (retic count<1%).
Figure 1E:
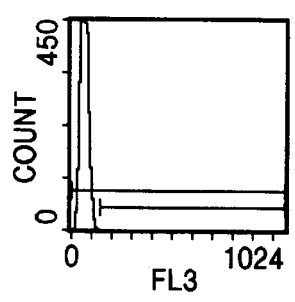
Figure 1F:
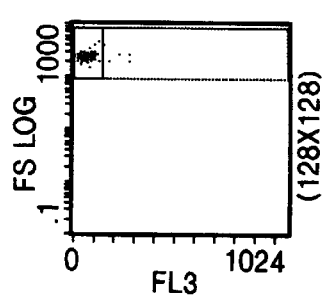
Figure 1G:
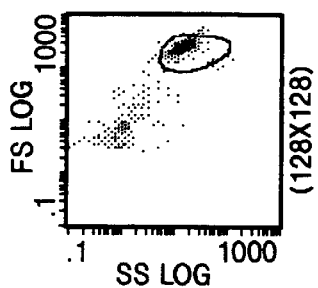
FIGS. 1G–1I show the fluorescence signals from reticulocyte for a sample with a medium reticulocyte count using TO-PRO-3 fluorescence (7% retic).
Figure 1H:
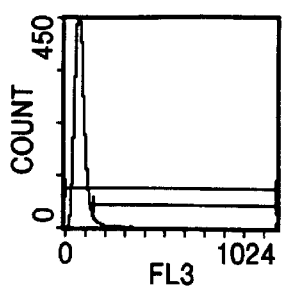
Figure 1I:
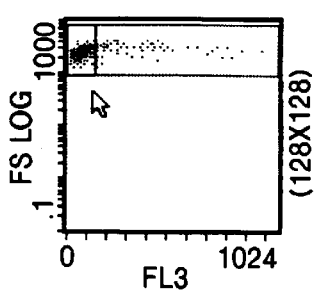
Figure 2A:
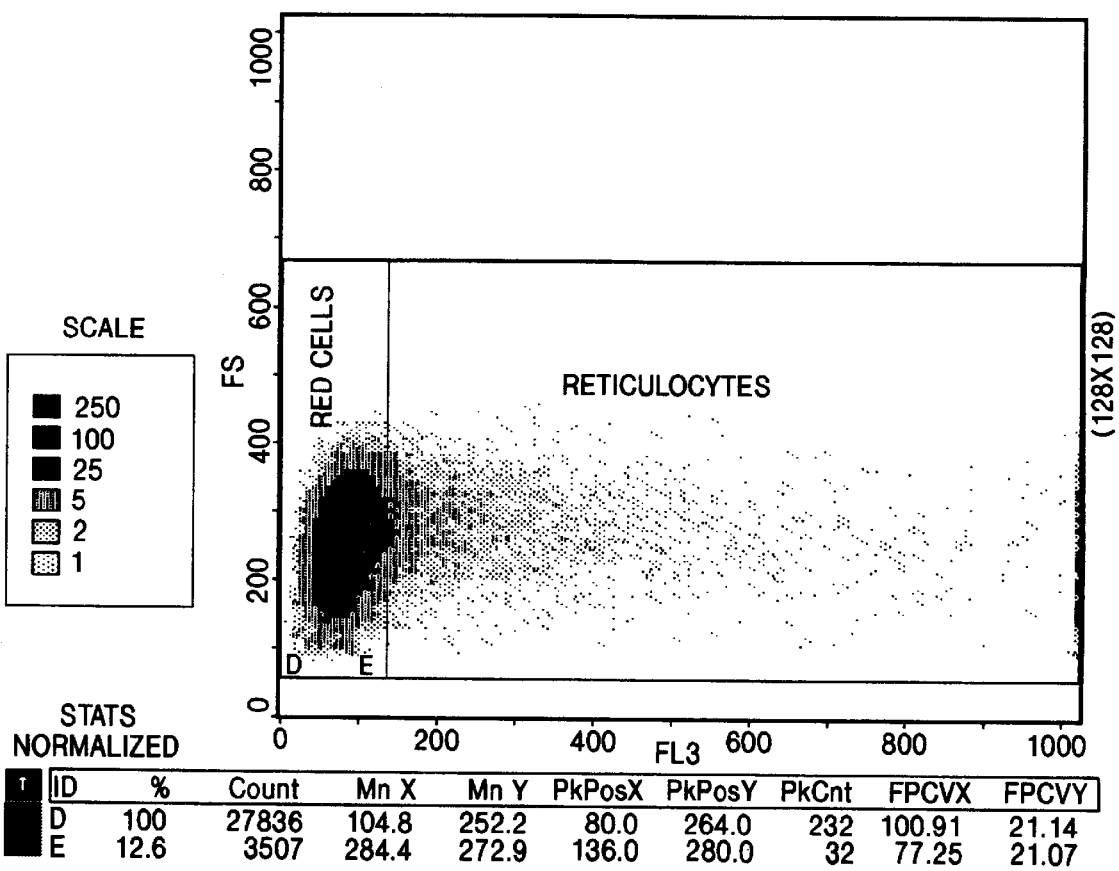
FIG. 2A shows the enumeration of reticulocytes by fluorescence. Reticulocytes are characterized by fluorescence signals from RNA-bound TO-PRO-3 molecules. The box on the right hand side defines the region in which reticulocytes are resolved from mature red cells.
Figure 2B:
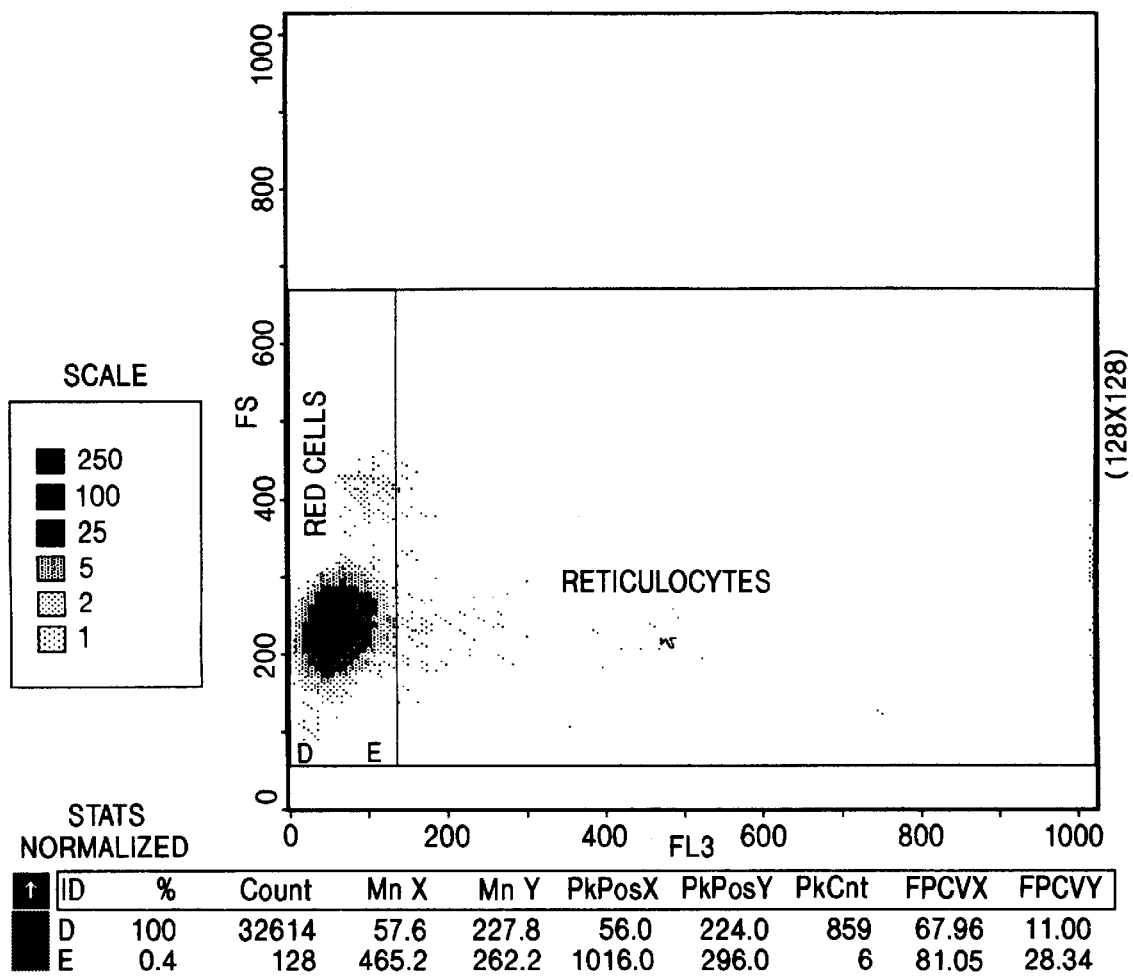
FIG. 2B shows sample with low reticulocyte count. Notice that with the same fixed region for reticulocytes as in FIG. 2A above, there are clearly fewer cells for this sample.

The present invention provides methods and compositions for facilitating rapid transport of nucleic acid dye molecules through cell membranes. Suitable samples containing cell populations for analyses are preferably selected from among whole blood samples and red blood cells. However, it may be desirable in certain circumstances to apply the method of the invention to white blood cells, peripheral blood lymphocytes, and cells derived from tissue and biopsy samples.

Advantageously, the method and compositions of the invention do not require cell fixation. Therefore, the method and composition of the invention are particularly well suited for use in analyses of living cells. However, selection of the cell population is not a limitation on the present invention.

The method of the invention involves the steps of contacting or mixing the cells with a dye which is a relatively cell impermeable dye in the presence of a non-ionic detergent and a sphering agent.

A great advantage of the method of the invention is the speed at which the staining is accomplished and the fact that it can be achieved in one step using whole blood. In contrast, prior art staining techniques for reticulocytes using Pyronin-Y require at least 2 hours or longer for fixation prior to staining and prior art staining techniques for reticulocyte detection using TO-PRO-3 require at least a 30 minute incubation period. In a currently preferred embodiment, the method of the invention requires only about one minute to stain reticulocytes.

Thus, the method of the invention facilitates rapid transport of nucleic acid dyes which are not readily cell membrane permeant in the time frame which is desirable for automated flow cytometry. As used herein, rapid transport refers to the ability of molecules to cross a cell membrane in less time than is required using the methods known in the art. Generally, rapid transport indicates that the molecule, when using the methods and/or compositions of the invention, permeate a cell membrane in less than 30 minutes, more preferably less than 10 minutes, and most preferably less than 5 minutes. Most desirably, the invention provides transport for the selected molecule across the cell membrane in about one minute. However, one of skill in the art can adjust this time as needed as desired, e.g., by increasing incubation time to 90 second or decreasing incubation time, e.g., to about 30 seconds.

An example of a currently preferred cell membrane impermeant dye is TO-PRO-3, which is described in U.S. Pat. No. 5,563,070. This dye and other dyes described in the '070 patent are commercially available from Molecular Probes, Inc. Other suitable dyes include other cell-impermeant dyes within the red, green or blue-excited wavelength regions. Examples of such dyes are described in U.S. Pat. No. 5,563,070 and include, TOTO-1, TOTO-3, POPO-3, PO-PRO-3, YOYO-1 or YO-PRO-1. Yet other suitable dyes may be readily selected from among propidium iodide, ethidium bromide, among others which are known and/or commercially available (e.g., from the Molecular Probes catalog). As defined herein, Pyronin Y [Sigma P9172] is also considered cell impermeable, as it requires cell fixation for between 30 minutes to about 2 hours prior to staining. In one preferred embodiment, the method and composition of the invention permits these previously cell membrane impermeant dyes to stain the intracellular nucleic acids in about one minute.

The method of the invention may also be useful for facilitating transport of other molecules across the cell membrane. Of particular interest are cell permanent dyes and other molecules which are useful in flow cytometry analyses, e.g., antibodies, enzyme substrates, DNAse, RNAse, and the like.

The method of the invention involves mixing the selected cells with a detergent, sphering agent, and a dye and permitting the cells to incubate in the presence of this cocktail for a suitable period of time, e.g., about one minute. However, if desired for purposes of convenience, this incubation period may be extended. Desirably, this mixing and incubation may be performed at room temperature. However, temperatures ranging from 18° C. to 40° C., may be utilized.

This method may be performed by contacting the selected cell with a single composition containing the detergent, sphering agent and dye. Alternatively, one of these components may be separately delivered to the cell.

Thus, a composition of the invention may contain a detergent and sphering agent. Alternatively, a composition of the invention may contain a detergent and the dye. In yet another alternative, a composition of the invention may contain the sphering agent and dye.

Suitable detergents may be readily selected from among non-ionic detergents. Desirably, these detergents are used at a concentration between about 0.001% to about 0.1%. One currently preferred detergent is Nonidet P-40. Examples of other suitable detergents include Igepal (Sigma CA-630) and Triton X (Sigma T9284). Other suitable detergent may be readily selected by one of skill in the art. Typically, these detergents are mixed into a sample (or vice versa), e.g., 1 mL of whole blood or the like.

A sphering agent may be readily selected by one of skill in the art. Desirably, the sphering reagent is a zwitterionic surfactant which isovolumetrically spheres the red blood cells and reticulocytes. The zwitterionic sphering agent is preferably an alkyl amido betaine or an alkyl betaine such as lauroamidopropylbetaine, cocoamidopropylbetaine and cocoamidosulfobetaine. Other sphering agents are N-tetradecyl-N-,N-dimethyl-3-ammonio-1- propanesulfonate and N-dodecyl-N,N-dimethyl-3-ammonio-1-propanesulfonate. See, U.S. Pat. No. 5,633,167 and U.S. Pat. No. 5,438,003. Currently, a preferred sphering reagent is dodecyl-β-D-maltoside, which suitably is in solution with a buffer such as phosphate buffered saline. To effectively isovolumetrically sphere the reticulocytes and red blood cells within a blood sample, the concentration of the sphering agent in the composition is most preferably from about 3 μg/ml to about 50 μg/ml with a mOSm of 290±5 mOSm. However, one of skill in the art may readily adjust this concentration as needed or desired.

Thus, the composition of the invention may further comprise other components, such as buffers, preservatives and the like. Suitable buffers include those which maintain the pH of the composition in the range of about 6 to about 9, for example, phosphate buffered saline or isotonic saline, such as ISOTON®II diluent, U.S. Pat. No. 3,962,125, Coulter Corporation, Miami, Fla., or the like. Selection of an appropriate buffer is not a limitation on the present invention.

Reticulocytes stained with TO-PRO-3, or another dye, according to the method of the invention, are preferably enumerated in an automatic flow cytometer. However, these cells may also been counted by a manual procedure or automated microscopy.

Automatic flow cytometers are well known in the art, and the present invention is not limited to the use of any particular flow cytometer. However, when TO-PRO-3, is used as the dye, the present invention advantageously permits the use of a red laser as an excitation source. Suitable excitation wavelengths may be readily determined by one of skill in the art. However, examples of suitable excitation wavelengths in the red range include those in the range of 600 nm to 700 nm, and preferably 630 nm to 670 nm. Other suitable excitation sources and wavelengths may be readily selected by one of skill in the art, taking into consideration the dye selected for use in the method and compositions of the invention. Selection of suitable light sources, and appropriate excitation wavelengths, are not a limitation on the present invention.

For example, reticulocytes stained with TO-PRO-3 according to the present invention may be detected and enumerated in a flow cytometer, such as the COULTER® XL™ flow cytometer [Coulter Corporation, Miami, Fla.]. In using such flow cytometers, light scatter gates are used to isolate red cells, and fluorescent gates are then used to delineate reticulocytes from mature red cells and enumerate.

In a currently preferred embodiment, the present invention provides a method for enumerating reticulocytes using TO-PRO-3, a sphering agent, and a strong, non-ionic detergent. Use of this composition is illustrated in the following examples.

TO-PRO-3 is a cell membrane impermeant dye. To stain intra-cellular nucleic acid with other membrane impermeant dyes, cell fixation has been used previously as a means to transport dye molecules to the interior of the cell. For example, cell fixation has been used as a means to stain intra-cellular RNA in reticulocytes with membrane impermeant dyes such as Pyronin Y [Tanke et al, cited above]. Therefore, using reference samples containing known reticulocyte percentage, an attempt was first made to fix the red cells with 7% formaldehyde prior to staining with TO-PRO-3. Cells thus fixed were treated to various concentrations of TO-PRO-3 and incubated for 30 min each. However, flow cytometric analysis of these cells showed no evidence of fluorescence due to nucleic acid staining. This result was unexpected, particularly in view of the fact that fixed human white blood cells as well as Chinese Hamster Ovary cells (CHO) stained with TO-PRO-3 and demonstrated bright red fluorescence from the dye in the 660 nm band, indicative of binding to intra-cellular DNA. Absence of nucleic-acid-bound TO-PRO-3 fluorescence from fixed reticulocytes indicated that, for reticulocytes, membrane transport problem for this dye could not be solved by the aforementioned fixation method.

The present invention permits reticulocytes to be stained in whole blood with TO-PRO-3 for subsequent flow analysis. The method of the invention differs from both the prior art pyronin-Y [Tanke et al, cited above] staining procedure requiring fixation of the cells and the prior art fluorescence staining procedures involving membrane permeable dyes such as CPO or acridine orange that requires no reagent other than the dye to accomplish the staining. For TO-PRO-3, fixation by formaldehyde did not produce any measurable staining of reticulocytes. However, permeabilising the cell membrane using a combination of detergent and sphering agent in presence of the dye according to the present invention resulted in efficient staining.

Another notable advantage of the preferred embodiment of the invention which utilizes TO-PRO-3 is that it permits the use of a less expensive excitation source than argon lasers used for all other presently available reticulocyte dyes, such as CPO, AO [Seligman, *Am. J. Hematology*, 14:57 91983)], TO [Lee et. al., Cytometry, 7:508 (1986)] and pyronin-Y. Specifically, a red diode laser, a high power light emitting diode (LED), or a red helium-neon laser can be used to conduct reticulocyte counting using TO-PRO-3. See, U.S. Pat. No. 5,563,070.

An additional advantage comes from the fact that TO-PRO-3 is essentially non-fluorescent in the unbound state. As a result, problems associated with background fluorescence is minimal, and reticulocytes can be detected with high specificity using this dye.

The following examples are provided to illustrate the invention and do not limit the scope thereof. One skilled in the art will appreciate that although specific reagents and conditions are outlined in the following examples, modifications can be made which are meant to be encompassed by the spirit and scope of the invention.

EXAMPLE 1

Materials and Methods

A. Spectroscopy 1 mM stock solution of TO-PRO-3 (Molecular Probes) in DMSO was purchased from Molecular Probes, Inc. For spectroscopic measurements, a dilute solution (concentration 1 μM) in PBS was prepared from this stock solution. 1.5 ml of the 1 μM solution was placed in a glass cuvette (Model 888-0105, Sienco, Wheat Ridge, Colo.) and fluorescence spectrum of the sample was measured using a spectrophotometer (Shimadzu Scientific Instruments, Inc.), with the sample excited at 633 nm. Next, a 1 μM solution of TO-PRO-3 was prepared from the stock solution by adding a 1 mg/ml solution of calf thymus DNA (Sigma) dissolved in PBS. After approximately 5 seconds the emission spectrum of this DNA+dye solution was measured, excitation wavelength being 633 nm. Finally, a 1 μM solution of TO-PRO-3 was prepared from the stock solution by adding solution of excess T-RNA (Sigma) dissolved in PBS and emission spectrum of the sample measured, also excited at 633 nm. These experiments demonstrated that TO-PRO-3, when bound to RNA, fluoresces brightly in a similar fashion as DNA-bound TO-PRO-3. This indicated that TO-PRO-3 can be a viable marker for detecting RNA in cells. The challenge was to determine a method to rapidly transport the dye through cell membrane to the intracellular RNA.

B. Flow Cytometry

Two different XL™ flow cytometers were used to conduct experiments described herein using TO-PRO-3 and CPO respectively. For TO-PRO-3 based measurements, an XL flow cytometer was equipped with a HeNe laser (633 nm) with approximately 11.5 mW power incident on the beam shaping optics. Forward light scatter (FS), side scatter (SS) and one fluorescence (FL) parameter in the orthogonal direction were measured to analyze the red cells. TO-PRO-3 fluorescence was measured at about 660 nm. The red cells were gated on a SS vs. FS dotplot. A fixed gate was then used to enumerate retics on a FL vs. FS dotplot.

For CPO based fluorescence measurements, a standard XL flow cytometer with a 488 nm argon laser was used as the illumination source. Forward scatter, side scatter and two fluorescence parameters were measured to analyze the red cells stained with CPO. The two fluorescence parameters corresponded to RNA-bound CPO fluorescence at 675 nm and DNA bound CPO fluorescence at 525 nm. The red cells were gated on a SS vs FS dotplot. An automated gating algorithm, available in commercial XL flow cytometers, calculated reticulocyte percentage from a DNA vs. RNA fluorescence dotplot.

EXAMPLE 2

Rapid Staining of Reticulocytes with Cell Impermeable Dye

1 $\mu$l of whole blood was added to 1 ml of a solution consisting of a "sphering reagent" that spheres red cells, detergent Nonidet P-40 (Sigma #N-6507) at a concentration of 0.01% and 1 $\mu$M TO-PRO-3 dye (Molecular Probes #T3605), and incubated for one minute. The sample was then analyzed in a XL flow cytometer modified to incorporate a red HeNe laser (632.8 nm). The sphering reagent is a solution of 20±3 $\mu$g/ml Dodecyl-$\beta$-D-maltoside/0.05% Proclin 300 in PBS at pH 7.4±0.1 and 290±5 mOsm.

When whole blood so treated with TO-PRO-3 in the presence of both a sphering reagent and the detergent Nonidet P-40, was analyzed in flow using 632.8 nm excitation, bright red fluorescence in the 660 band resulted from a population of red cells, and indicated the presence of nucleic acid bound TO-PRO-3 in such cells. This fluorescence was attributed to TO-PRO-3 stained reticulocytes. The distribution of the cells in a forward scatter versus fluorescence dotplot was consistent with the distribution of mature red cells and reticulocytes previously shown by Tanke et. al. [cited above] in relation to their work on Pyronin Y based reticulocyte measurements. Further, the percentage of the fluorescent subpopulation corresponded closely to reticulocyte percentage for each sample enumerated by independent measurements based on CPO fluorescence in a standard XL flow cytometer.

EXAMPLE 3

Staining of Reticulocytes with Cell Impermeable Dye

To investigate the individual effects of the sphering reagent and the detergent Nonidet P-40 in the experiment of Example 2, samples were also prepared by adding 1 $\mu$l whole blood to 1 $\mu$M TO-PRO-3 in 1 ml of the sphering reagent and to 1 $\mu$M TO-PRO-3 in 1 ml of PBS containing 0.01% Nonidet P-40 separately, and each incubated for 1 min. Samples, thus prepared, were then analyzed in a XL flow cytometer with 632.8 nm excitation.

TO-PRO-3 in the sphering reagent alone did not result in appreciable staining and TO-PRO-3 in 0.01% Nonidet P-40 resulted in marginal staining.

The reticulocyte analysis of whole blood treated with TO-PRO-3 under different conditions: (a) Cells treated with TO-PRO-3 alone: Total count 32954, Red cells 28168, Reticulocytes 196, calculated retic percentage 0.7%; (b) Cells treated with TO-PRO-3 in presence of the sphering agent was as follows: Total count 33819, Red cells 29038, Reticulocytes 291, calculated retic percentage 1.0%; (c) fluorescence intensity for cells treated with TO-PRO-3 in presence of detergent Nonidet P-40 was as follows: Total count 32659, Red cells 27903, Reticulocytes 1324, calculated retic percentage 4.7%. The fluorescence intensity for cells treated with TO-PRO-3 in presence of detergent Nonidet P-40 and sphering agent was as follows: Total count 32887, Red cells 28156, Reticulocytes 3753, calculated retic percentage 13.3%. See, FIGS. 3A–3D.

This experiment clearly demonstrated that the combination of sphering agent and detergent was the most effective in facilitating TO-PRO-3 staining of intracellular RNA in reticulocytes.

EXAMPLE 4

Comparative Example

For comparison, an alternative staining procedure described in literature by Yamamoto et. al. [cited above] was investigated. In accordance with this procedure, 5 $\mu$l whole blood was incubated in 1 ml PBS containing 50 $\mu$M TO-PRO-3 for 30 min, after which the sample was analyzed by a flow cytometer with 633 nm excitation. This experiment was further repeated by varying incubation times (1, 10, 20, and 30 minutes).

Finally, for reference, each sample of blood was analyzed by known reticulocyte detection/enumeration procedure using CPO [Shenkin, U.S. Pat. No. 5,639,666] as the retic stain excited at 488 nm. In this procedure, sample was prepared by incubating 1 $\mu$l whole blood in 1 ml CPO reagent (8 $\mu$g/ml) for 30 min. A well behaved trend is observed in the correlation between the two sets of results (FIG. 4).

Fluorescence from reticulocytes under various staining conditions was demonstrated for a blood sample that was known to contain a relatively high reticulocyte percentage. It is clear from this data (not shown here) that the method described in Yamamoto did not stain the reticulocytes appropriately. This is not surprising, in view of the fact that TO-PRO-3 is membrane impermeant. Increasing the incubation time further also did not seem to result in any improvement of staining by that method.

EXAMPLE 5

Rapid Staining of Reticulocytes with Cell Impermeable Dyes

A. Propidium Iodide

1 $\mu$l of whole blood was added to 1 ml of a solution consisting of a "sphering reagent" that spheres red cells, 0.01% detergent Nonidet P-40 (Sigma), and propidium iodide (50 $\mu$g/ml) and incubated for one minute. The sample was then analyzed in a XL flow cytometer using an argon laser (488 nm). The sphering reagent is a solution of 20±3 $\mu$g/ml Dodecyl-$\beta$-D-maltoside/0.05% Proclin 300 in PBS at pH 7.4±0.1 and 290±5 mOsm.

A bright red fluorescence resulted from a population of red blood cells, and indicated the presence of nucleic acid bound propidium iodide in such cells. This fluorescence was attributed to propidium iodide stained reticulocytes.

B. TOTO-1

1 $\mu$l of whole blood was added to 1 ml of a solution consisting of a "sphering reagent" that spheres red cells, 0.01% Nonidet P-40 (Sigma), and 1 $\mu$M TOTO-1 dye [Molecular Probes, cat#T3600] and incubated for one minute. The sample was then analyzed in a XL flow cytometer using an argon laser (488 nm). The sphering reagent is a solution of 20±3 mg/ml Dodecyl-β-maltoside/0.05% Proclin 300 in PBS at pH 7.4±0.1 and 290±5 mOsm.

A bright green fluorescence resulted from a population of red blood cells, and indicated the presence of nucleic acid bound TOTO-1 in such cells. This fluorescence was attributed to TOTO-1 stained reticulocytes.

All publications cited in this specification are incorporated herein by reference herein. While the invention has been described with reference to a particularly preferred embodiment, it will be appreciated that modifications can be made without departing from the spirit of the invention. Such modifications are intended to fall within the scope of the appended claims.

What is claimed is:

1. A method for facilitating rapid transport of dye molecules through a cell membrane comprising the steps of contacting a cell sample with a mixture consisting of a cell membrane impermeant dye, a non-ionic detergent and a sphering agent.

2. The method according to claim 1, further comprising the step of incubating the sample with the dye, detergent and sphering agent for about one minute.

3. The method according to claim 1, wherein the dye is selected from the group consisting of TO-PRO-3, TOTO-1, TOTO-3, POPO-3, PO-PRO-3, YOYO-1, YO-PRO-1, propidium iodide, ethidium bromide, and Pyronin Y.

4. The method according to claim 1, wherein the detergent is selected from the group consisting of Nonidet P-40, Igepal, and Triton X.

5. The method according to claim 1, wherein the sphering agent comprises a solution of dodecyl-β-D-maltoside and Proclin 300.

6. The method according to claim 1, wherein the sample comprises cells which are living and are not fixed.

7. A method for staining nucleic acids in a cell using a cell membrane impermeant dye, said method comprising the steps of:

(a) providing a sample comprising a cell; and (b) contacting the sample with a mixture consisting of a non-ionic detergent, a sphering agent and a cell membrane impermeant dye for nucleic acids.

8. The method according to claim 7, wherein the sample comprises cells which are living and not fixed.

9. The method according to claim 8, wherein the nucleic acids are inside reticulocytes.

10. A method for rapid analysis of reticulocytes with a cell impermeable dye comprising the steps of: (a) contacting a cell sample containing reticulocytes with a mixture consisting of a cell impermeable dye, a non-ionic detergent and a sphering agent; and (b) analyzing the cells by automated flow cytometry to detect the presence of stained reticulocytes.

11. The method according to claim 10, further comprising the step of incubating the cells with the dye, detergent and sphering agent for about one minute prior to analyzing the cells.

12. The method according to claim 10, wherein the sample comprises whole blood.

13. The method according to claim 10, wherein the dye is TO-PRO-3 and the reticulocytes are analyzed using a red laser as an excitation source.

14. A composition which facilitates transport of cell impermeable dye molecules through cell membrane; said composition consisting of a non-ionic detergent, a sphering agent, and cell impermeable dye molecule.

15. The composition according to claim 14, wherein said dye is selected from the group consisting of TO-PRO-3, TOTO-1, TOTO-3, POPO-3, PO-PRO-3, YOYO-1, YO-PRO-1, propidium iodide, ethidium bromide, and Pyronin Y.

16. The composition according to claim 14 wherein the sphering agent is a zwitterionic detergent.

* * * * *